United States Patent [19]

Schmahmann

[11] Patent Number: 5,211,630
[45] Date of Patent: May 18, 1993

[54] HYPODERMIC SYRINGE

[76] Inventor: David R. Schmahmann, 50 Longwood Ave. #815, Brookline, Mass. 02146

[21] Appl. No.: 895,617

[22] Filed: Jun. 9, 1992

[51] Int. Cl.$^5$ .............................................. A61M 5/00
[52] U.S. Cl. ...................................... 604/110; 604/195
[58] Field of Search .............. 604/110, 187, 198, 263, 604/218, 195, 192

[56] References Cited

U.S. PATENT DOCUMENTS

| 2,674,246 | 4/1954 | Bower. | |
|---|---|---|---|
| 4,425,120 | 1/1984 | Sampson et al. | 604/198 |
| 4,631,057 | 12/1986 | Mitchell | 604/198 |
| 4,723,943 | 2/1988 | Spencer | 604/198 |
| 4,737,144 | 4/1988 | Choksi | 604/198 |
| 4,738,663 | 4/1988 | Bogan | 604/198 |
| 4,826,491 | 5/1989 | Schramm | 604/198 |
| 4,846,796 | 7/1989 | Carrell et al. | 604/110 |
| 4,874,383 | 10/1989 | McNaughton | 604/198 |
| 4,921,486 | 5/1990 | DeChellis et al. | 604/110 |
| 4,943,282 | 7/1990 | Page et al. | 604/198 |
| 5,114,410 | 5/1992 | Batlle | 604/195 |

Primary Examiner—John D. Yasko
Attorney, Agent, or Firm—Lorusso & Loud

[57] ABSTRACT

A hypodermic syringe having means for moving the needle, upon completion of usage, from a working position outside the barrel portion of the syringe to a disposal position inside the barrel portion, to prevent inadvertent contact of an operator with the used needle.

16 Claims, 7 Drawing Sheets

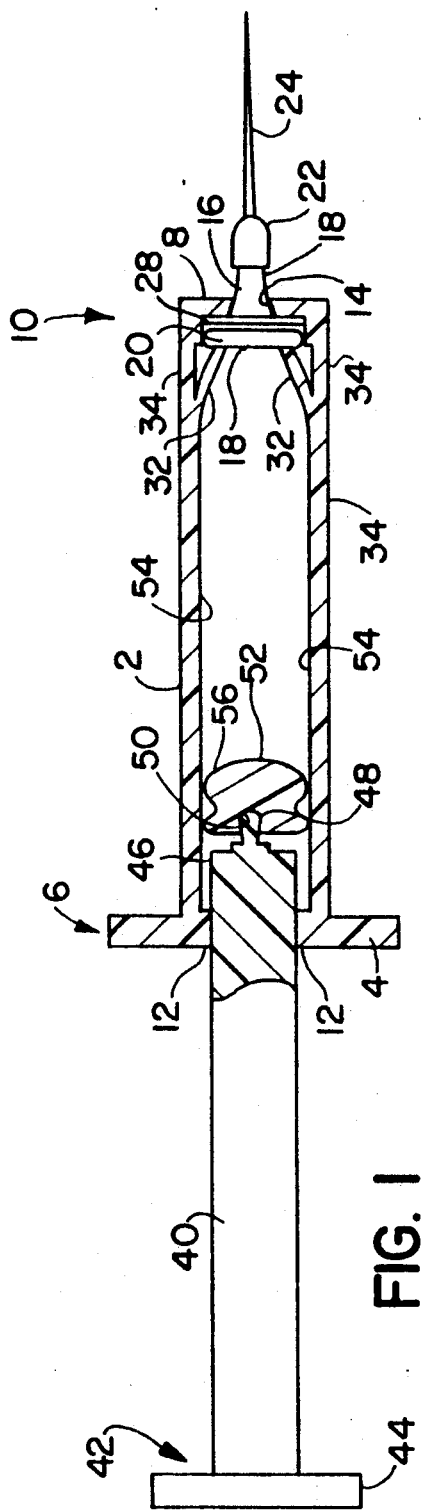
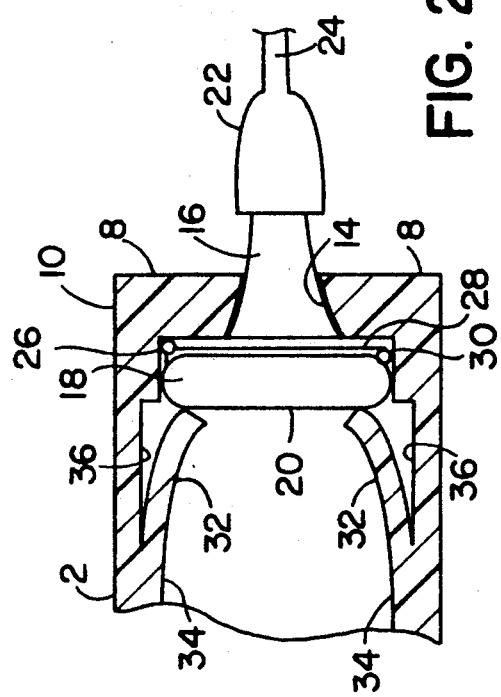

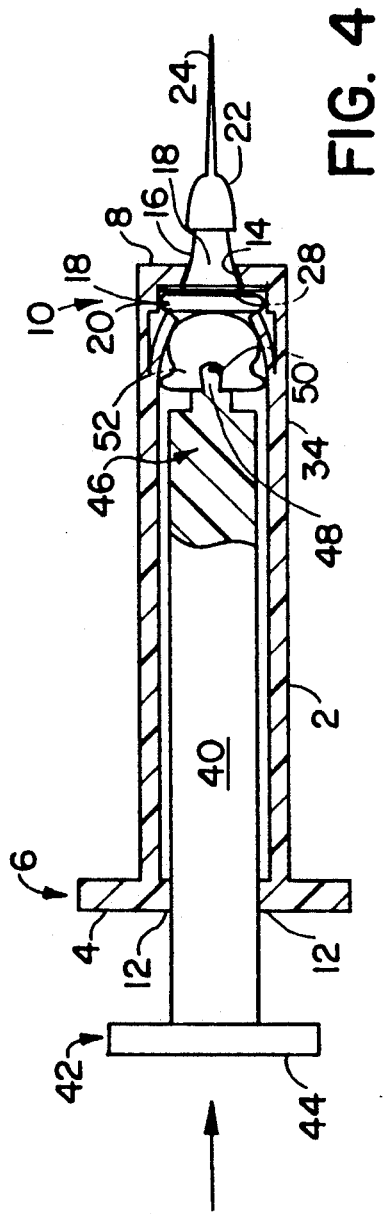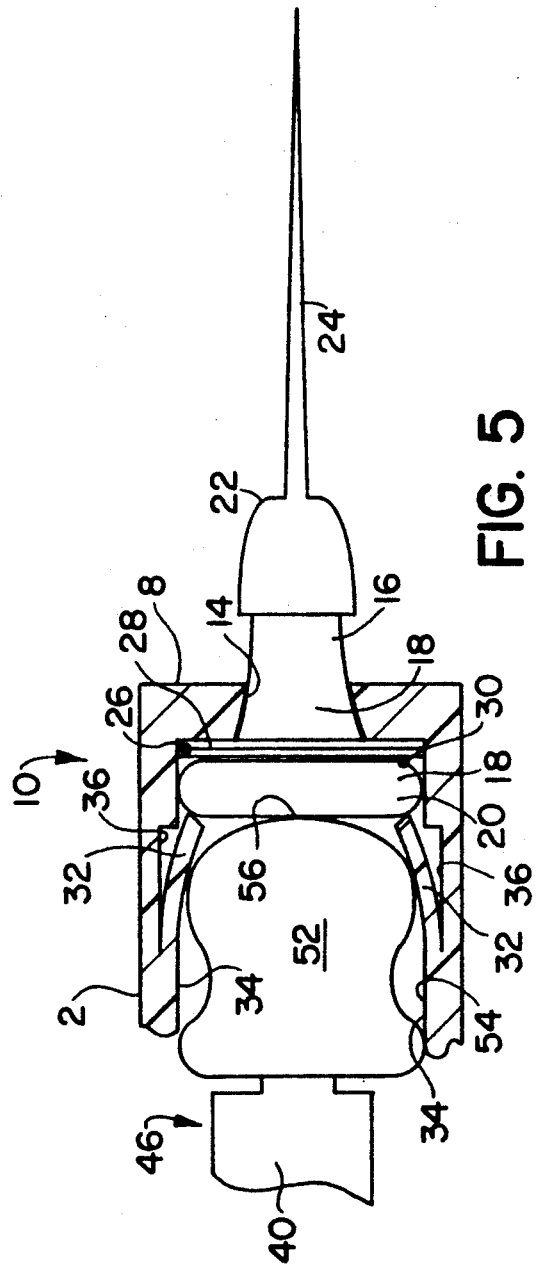

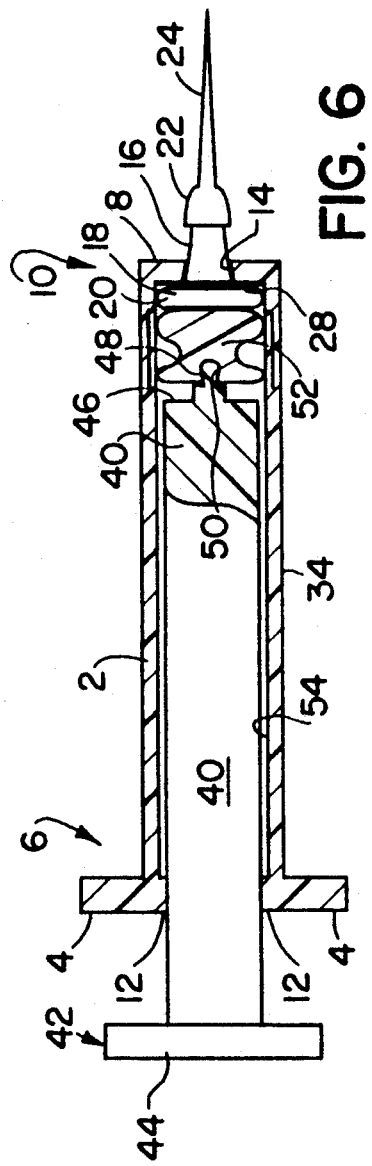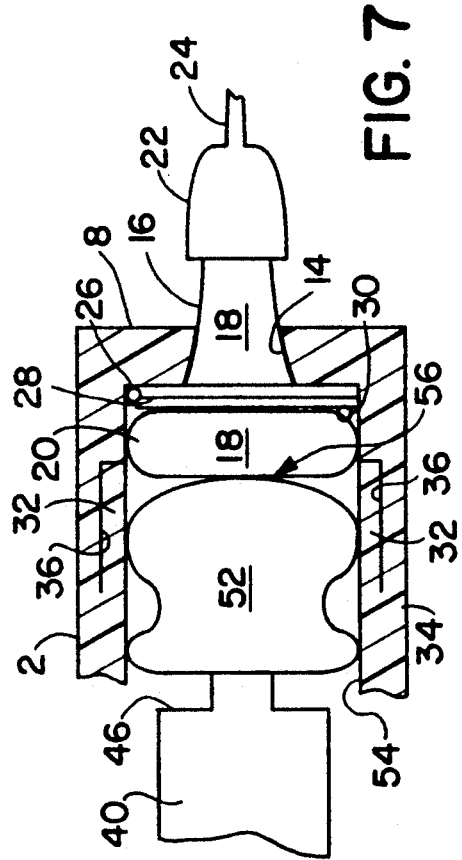

HYPODERMIC SYRINGE

BACKGROUND OF THE INVENTION

1. Field of the Invention

This invention relates to hypodermic syringes and is related more specifically to a hypodermic syringe having means for retracting the needle, after use, from a working position outside of the barrel of the syringe to a disposal position within the barrel, to avoid inadvertent contact of an operator with the used needle.

2. Description of the Prior Art

Shielding of needles of used hypodermic syringes is generally known. In U.S. Pat. No. 4,425,120, issued Jan. 10, 1984, in the names Norma A., Sampson, et there is disclosed a syringe having a tubular needle guard slidably mounted on the barrel, such that the guard may be moved to an extended position in which the guard shields the needle and to a retracted position in which the guard does not shield the needle.

Other patents showing syringes having tubular needle guards slidable on the syringe barrel from a position removed from the needle to a position covering the needle include U.S. Pat. No. 4,631,057, issued Dec. 23, 1986, in the name of Charles B. Mitchell; U.S. Pat. No. 4,723,943, issued Feb. 9, 1988, in the name of John E. Spencer; U.S. Pat. No. 4,737,144, issued Apr. 12, 1988, in the name of Pradip V. Choskie; U.S. Pat. No. 4,738,663, issued Apr. 19, 1988, in the name of David B. Bogan; U.S. Pat. No. 4,826,491, issued May 2, 1989, in the name of James E. Schramm; U.S. Pat. No. 4,846,796, issued Jul. 11, 1989, in the name of Michael W. Carrell, et al.; U.S. Pat. No. 4,874,383, issued Oct. 17, 1989, in the name of R. David McNaughton; and U.S. Pat. No. 4,943,282, issued Jul. 24, 1990, in the names of Mary J. Page, et al.

While the syringes of the type covered by the above patents provide means for shielding a syringe needle after use, the use of a sleeve slidable upon the syringe barrel renders the syringe, in the needle-exposed condition, necessarily larger in diameter than would be the case with the barrel only, resulting in a bulkier tool for hand manipulation. In the needle-covered condition, the length of the barrel is substantially doubled by the extended position of the shielding sleeve, resulting in a bulkier package to be disposed of.

It would be beneficial to have available a hypodermic syringe having facility for safely shielding the used needle of the syringe, but not with the attendant bulkiness, both during use and in disposal, of the shielding guard sleeve known in the art.

SUMMARY OF THE INVENTION

It is, therefore, an object of the invention to provide a hypodermic syringe having means for safely covering a used needle, but without a tubular shield mounted on the barrel of the syringe.

With the above and other objects in view, as will hereinafter appear, a feature of the present invention is the provision of a hypodermic syringe comprising a barrel, a plunger slidably disposed in the barrel and extending from a proximal end of the barrel, a stopper mounted on a first end of the plunger, a needle mounting member disposed in the barrel, a portion of the needle mounting member being adapted to extend through an opening in a distal end of the barrel, a needle mounted on the needle mounting member portion, a coil spring fixed at one end to an internal portion of the barrel proximate the distal end thereof and fixed at a second end to the needle mounting member, and leaf spring means extending inwardly of the barrel from wall potions of the barrel and adapted to engage the needle mounting member to hold the needle mounting member adjacent the distal end of the barrel against the bias of the coil spring, the stopper being adapted to urge the leaf spring means outwardly to disengage from the needle mounting member, to permit the needle mounting member and the needle to move in the barrel toward the proximal end of the barrel to move the needle from outside the barrel to inside the barrel.

The above and other features of the invention, including various novel details of construction and combinations of parts, will now be more particularly described with reference to accompanying drawings and pointed out in the claims. It will be understood that the particular device embodying the invention is shown by way of illustration only and not as a limitation of the invention. The principles and features of this invention may be employed in various and numerous embodiments without departing from the scope of the invention.

BRIEF DESCRIPTION OF THE DRAWINGS

Reference is made to the accompanying drawings in which is shown an illustrative embodiment of the invention, from which its normal features and advantages will be apparent.

In the drawings:

FIG. 1 is a partly side elevational, partly centerline sectional, view of one form of hypodermic syringe illustrative of an embodiment of the invention;

FIG. 2 is an enlarged view of a portion of the syringe shown in FIG. 1;

FIG. 3 is similar to FIG. 1, but shows a plunger moving in a barrel portion of the syringe, as in administering an inoculation, or the like;

FIG. 4 is similar to FIG. 3, but shows a stopper portion mounted on the plunger having reached the distal end of the barrel;

FIG. 5 is an enlarged view of a portion of the syringe shown in FIG. 4;

FIG. 6 is similar to FIG. 4, but shows the stopper portion pressed further into the distal end of the barrel;

FIG. 7 is an enlarged view of a portion of the syringe shown in FIG. 6;

DESCRIPTION OF THE PREFERRED EMBODIMENT

Figure 3:
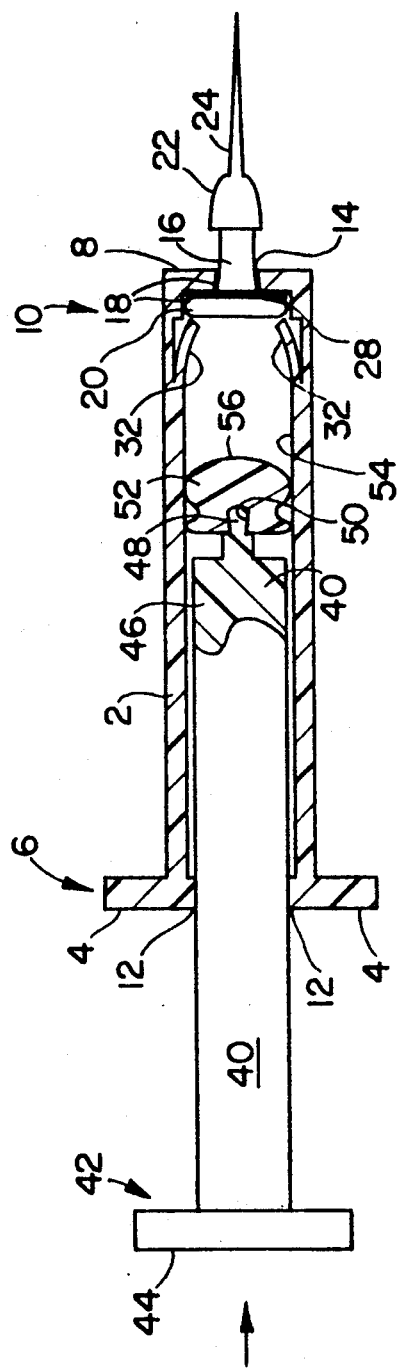

Referring to FIG. 1, it will be seen that an illustrative embodiment of the hypodermic syringe includes a barrel 2 having opposed outwardly directed flanges 4 at a proximal end 6 thereof, and an end wall 8 at a distal end 10 thereof. At the proximal end 6 of the barrel 2, there are disposed inwardly projecting stops 12.

Referring to FIGS. 1 and 2, it will be seen that at the distal end 10 of the barrel 2, the end wall 8 is provided with a central opening 14 adapted to receive a generally frusto-conically shaped post portion 16 of a needle mounting member 18. In addition to the portion 16, the needle mounting member 18 includes a disc portion 20 from which extends the frusto-conically shaped portion 16.

The frusto-conically shaped portion 16 of the needle mounting member 18 is adapted to receive and retain a needle mounting cup 22 from which extends a needle 24.

To the barrel distal end wall 8 there is connected, as at location 26 (FIG. 2) a first end of an elliptically wound coil spring 28, and to the disc portion 20 of the needle mounting member 18 there is connected, as at location 30, a second end of the coil spring 28.

The barrel 2 is of a plastic material and has internally thereof leaf springs 32, directed inwardly from walls 34 of the barrel 2. Preferably, as shown in the drawings (FIG. 2), the leaf springs 32 are integral with the barrel walls 34 and adapted to be fitted within an area 36 (FIGS. 2 and 5) from which the leaf springs 32 are cut.

Slidably movable within the barrel 2 is a plunger 40 having at a proximal end 42 thereof a pusher member 44. At a distal end 46 of the plunger 40, there is provided an extension, such as a knob 48 fitted into a cavity 50 of a stopper 52 which is thereby mounted on the distal end 46 of the plunger 40 and retained by friction. The plunger 40 rides on inner edges of the stops 12 and the stopper 52 rides along internal surfaces 54 of the barrel walls 34.

The stopper 52 is of domed configuration at its forward end 56 and is of an elastomeric material and therefore somewhat compressible axially and expandable radially.

As may be seen in FIG. 1, the syringe, when ready for administration to a patient, has the needle 24 attached to the needle mounting member 18. The disc portion 20 of the needle mounting member 18 is held adjacent the end wall 8 of the barrel 2 by the inwardly extending leaf springs 32 which abut the disc portion 20. The coil spring 28 is compressed between the disc portion 20 and the barrel end wall 8. Extending from the proximal end 6 of the barrel (FIG. 1) is the plunger 40, its distal end 46 being in the barrel 2 and having mounted thereon the stopper 52. The area in the barrel 2 between the stopper 52 and the disc portion 20 of the needle mounting member 18 is filled with a liquid medicament to be dispensed from the syringe.

To dispense the medicament from the barrel 2 (FIG. 3), the plunger 40 typically is pressed by an operator to move the stopper 52 along the internal surfaces 54 of the barrel wall 34. The plunger 40 slides along inward edges of the stops 12. Upon completion of the evacuation of the barrel 2, the stopper 52 comes to rest against the disc portion 20 of the needle mounting member 18 (FIGS. 4 and 5). At this point, the leaf springs 32 are deflected outwardly toward their respective recesses 36, but not necessarily entirely disengaged from the disc portion 20.

The operator, after completion of administering to the patient with the syringe, presses the plunger 40 firmly into the barrel 2 (FIGS. 6 and 7), causing the dome shaped stopper forward end 56 to move the disc portion 20 against the coil spring bias to disengage the disc from the leaf springs 32. The slight further movement of the plunger into the barrel also operates to axially compress the stopper 56 to cause the stopper to expand radially, or width-wise, of the barrel axis. Such width-wise expansion of the stopper 56 forces the leaf springs 32 into their respective recesses 36, permitting the coil spring to move the disc portion 20 into the elastomeric stopper 52 beyond the edges of the leaf springs 32.

Figure 8:
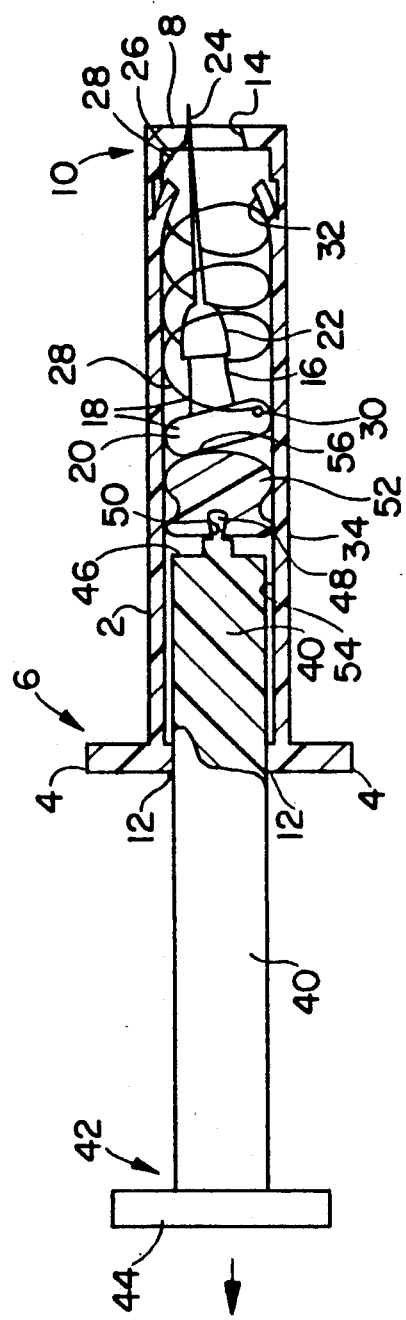
FIG. 8 is similar to FIG. 6, but shows the plunger being withdrawn from the distal end of the barrel and moved toward a proximal end of the barrel.

Movement of the plunger 40 rearwardly (FIG. 8), permits expansion of the coil spring 28 which operates to keep the disc portion 20 in contact with the moving stopper 52. As the needle mounting member 18 moves toward the proximal end 6 of the barrel, it carries with it the needle 24, which enters the barrel 2 through the barrel end wall opening 14. Because the coil spring 28 is elliptical, it tends to cause the needle mounting portion to assume a position at an other than normal angle to the axis of the barrel, as shown in FIG. 8, causing the needle 24 to slide into the barrel 2 along the edge of the barrel end wall opening 14.

Figure 9:
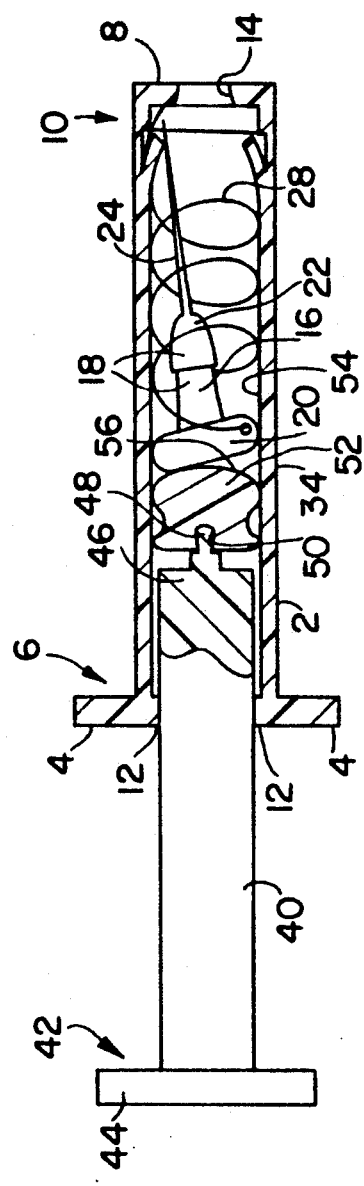
FIG. 9 is similar to FIG. 8, but shows the needle having been drawn into the barrel and biased by an elliptical coil spring into a storage position.
Figure 10:
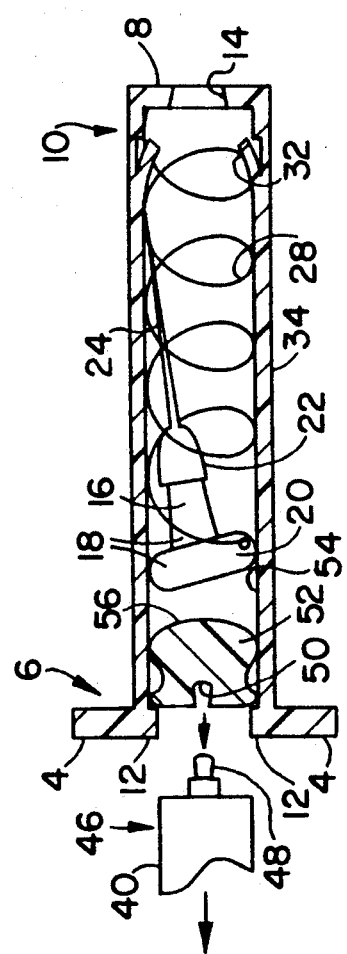
FIG. 10 is similar to FIG. 9, but shows the stopper disposed at the proximal end of the barrel and the plunger disengaged from the stopper.

Referring to FIG. 9, it will be seen that as soon as the needle 24 clears the opening 14, the elliptical coil spring 28 causes the disc portion 20 to move to a more angled position, relative to the axis of the barrel, and the needle 24 to essentially snap into a position placing the point of the needle in an area further removed from the opening 14. In due course, the stopper 52 encounters the barrel stops 12 (FIG. 10), which operate to retain the stopper in the proximal end 6 of the barrel 2. Continued pulling on the plunger 40 by the operator causes the plunger knob 48 to pop out of the cavity 50 in the elastomeric stopper 52, leaving the stopper in position closing the proximal end 6 of the barrel 2.

The barrel 2, with the needle 24 therein may then be discarded with the barrel serving as a guard, or shield, for the needle, The space required for the protected needle is roughly half of that required for the well known barrel and tubular guard combination.

It is to be understood that the present invention is by no means limited to the particular construction herein disclosed and/or shown in the drawings, but also comprises any modifications or equivalents within the scope of the claims.

Having thus described my invention, what I claim as new and desire to secure by Letters Patent of the United States is:

1. A hypodermic syringe comprising a barrel, a plunger slidably disposed in said barrel and extending from a proximal end of said barrel, a stopper mounted on a first end of said plunger, a needle mounting member disposed in said barrel, a post portion of said needle mounting member being adapted to extend through an opening in a distal end of said barrel, a needle mounted on said post portion, a coil spring fixed at one end to an internal portion of said barrel proximate a distal end wall thereof and fixed at a second end to said needle mounting member to bias said needle mounting member toward said proximal end of said barrel, and leaf spring means extending inwardly of said barrel from wall portions of said barrel and adapted to engage said needle mounting member to hold said needle mounting member adjacent said distal end of said barrel against said bias of said coil spring, said stopper being adapted to engage said leaf spring means to move said leaf spring means outwardly to disengage from said needle mounting member, to permit said needle mounting member and said needle to move in said barrel in response to said coil spring bias toward said proximal end of said barrel to move said needle from outside said barrel to inside said barrel.

2. The hypodermic syringe in accordance with claim 1 wherein said stopper moves in said barrel engaged with internal walls of said barrel.

3. The hypodermic syringe in accordance with claim 2 wherein said stopper has a doomed distal end adapted to engage said needle mounting member.

4. The hypodermic syringe in accordance with claim 1 wherein said needle mounting member includes a disc portion and said needle mounting member post portion extends from said disc portion.

5. The hypodermic syringe in accordance with claim 4 wherein said post portion is of a generally frusto-conical configuration.

6. The hypodermic syringe in accordance with claim 3 wherein said needle mounting member includes a disc portion from which extends said post portion, said stopper domed end being adapted to engage said disc to move said disc against said coil spring bias to disengage said disc from said leaf springs.

7. The hypodermic syringe in accordance with claim 2 wherein said stopper is of elastomeric material and is adapted to engage said needle mounting member to move said needle mounting member against said coil spring bias to disengage said needle mounting member from said leaf springs.

8. The hypodermic syringe in accordance with claim 1 wherein said stopper is releasably fixed to said plunger, and further comprising stop means internally of said barrel and adapted to engage said stopper and stop rearward movement of said stopper in said barrel.

9. The hypodermic syringe in accordance with claim 8 wherein said stopper is of elastomeric material and is provided with a cavity in a proximal end thereof, and said plunger is provided with a extension fitted in said cavity and retained in said cavity by friction, said extension being adapted to be withdrawn from said cavity upon further rearward movement of said plunger after said engagement of said stopper by said stop means.

10. The hypodermic syringe in accordance with claim 7 wherein said elastomeric stopper, upon said engagement with said needle mounting member, is adapted to compress axially and expand radially to effect said movement of said leaf spring means outwardly.

11. The hypodermic syringe in accordance with claim 1 wherein said leaf spring means comprise integral portions of said barrel wall portions and said barrel wall portions have recesses complementary to said spring means.

12. The hypodermic syringe in accordance with claim 1 wherein said coil spring is an elliptically-wound spring.

13. The hypodermic syringe in accordance with claim 4 wherein said second end of said coil spring is fixed to said disc portion and said coil spring is an elleiptically - wound spring.

14. The hypodermic syringe in accordance with claim 13 wherein said coil spring urges said disc portion to a position in which said disc portion is at an other than normal angle with respect to the axis of said barrel.

15. The hypodermic syringe in accordance with claim 14 wherein said needle, upon being drawn into said barrel, is adapted, in response to said movement of said disc portion by said coil spring, to move in said barrel such that a point of said needle is disposed in said barrel proximate a juncture of one of said barrel wall portions and said distal end wall of said barrel and removed from said opening in said barrel.

16. The hypodermic syringe in accordance with claim 13 wherein said second end of said coil spring is fixed to a peripheral portion of said disc portion.

* * * * *